US008808169B2

(12) United States Patent
Macnamara et al.

(10) Patent No.: US 8,808,169 B2
(45) Date of Patent: Aug. 19, 2014

(54) STEERING SYSTEM TENSION CONTROL DEVICES

(75) Inventors: Francis T. Macnamara, Newtown, MA (US); James Duronio, Westford, MA (US); Roy H. Sullivan, Millville, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 507 days.

(21) Appl. No.: 12/843,318

(22) Filed: Jul. 26, 2010

(65) Prior Publication Data

US 2011/0021875 A1 Jan. 27, 2011

Related U.S. Application Data

(62) Division of application No. 11/394,645, filed on Mar. 31, 2006, now abandoned.

(51) Int. Cl.
*A61B 1/00* (2006.01)
*A61B 1/005* (2006.01)

(52) U.S. Cl.
CPC .............. *A61B 1/0051* (2013.01); *A61B 1/0057* (2013.01); *A61B 1/005* (2013.01); *A61B 1/0052* (2013.01); *A61B 1/0053* (2013.01); *A61B 1/0056* (2013.01)
USPC ............................ 600/149; 600/148; 600/144

(58) Field of Classification Search
CPC .... A61B 1/005; A61B 1/0051; A61B 1/0052; A61B 1/0053; A61B 1/0056; A61B 1/0057
USPC ................... 600/146–150, 139–145
See application file for complete search history.

(56) References Cited

U.S. PATENT DOCUMENTS

| 4,294,233 | A | * | 10/1981 | Takahashi ..................... 600/149 |
| 4,432,349 | A | | 2/1984 | Oshiro |
| 4,483,326 | A | | 11/1984 | Yamaka et al. |
| 4,659,195 | A | | 4/1987 | D'Amelio et al. |
| 4,688,555 | A | | 8/1987 | Wardle |
| 4,748,969 | A | | 6/1988 | Wardle |
| 4,762,118 | A | | 8/1988 | Lia et al. |
| 4,762,119 | A | * | 8/1988 | Allred et al. ................... 600/149 |
| 4,787,369 | A | | 11/1988 | Allred, III et al. |
| 4,947,827 | A | * | 8/1990 | Opie et al. ...................... 600/108 |
| 5,005,558 | A | * | 4/1991 | Aomori .......................... 600/141 |
| 5,060,660 | A | | 10/1991 | Gambale et al. |
| 5,195,968 | A | | 3/1993 | Lundquist et al. |
| 5,299,559 | A | | 4/1994 | Bruce et al. |
| 5,331,948 | A | | 7/1994 | Utsumi et al. |

(Continued)

FOREIGN PATENT DOCUMENTS

EP 0 165 718 A2 12/1985
WO WO 93/20742 A1 10/1993

OTHER PUBLICATIONS

International Patent Application No. PCT/US2007/062995: International Search Report and Written Opinion; Date of mailing: Aug. 14, 2007.

*Primary Examiner* — Alireza Nia
(74) *Attorney, Agent, or Firm* — Bookoff McAndrews, PLLC

(57) ABSTRACT

A steerable shaft of a medical instrument is steered by one or more control cables. The control cables are in contact with a steering system tension control device that reduces the tension in the control cables caused by bends in the shaft.

18 Claims, 4 Drawing Sheets

(56) References Cited

U.S. PATENT DOCUMENTS

| | | |
|---|---|---|
| 5,448,989 A | 9/1995 | Heckele |
| 5,512,035 A | 4/1996 | Konstorum et al. |
| 5,531,664 A * | 7/1996 | Adachi et al. ............. 600/149 |
| 2004/0186350 A1 | 9/2004 | Brenneman et al. |

* cited by examiner

STEERING SYSTEM TENSION CONTROL DEVICES

This is a division of U.S. application Ser. No. 11/394,645, filed Mar. 31, 2006 now abandoned, which is incorporated herein by reference in its entirety.

FIELD OF THE INVENTION

The present invention relates to medical instruments in general, and to instruments with steerable shafts in particular.

BACKGROUND

As an alternative to performing more invasive medical procedures, many physicians are utilizing endoscopes and catheters to perform diagnostic and therapeutic procedures on the internal tissues of patients. With this less invasive approach, a medical instrument, such as an endoscope or a catheter is advanced to a site of interest in order to perform the indicated procedure. Most endoscopes and catheters have a flexible shaft that allows the endoscope or catheter to wind its way through bends in the patient's anatomy until it reaches the tissue of interest. In order to advance the flexible shaft, most steerable endoscopes have a system of control cables that act in pairs to help direct the distal tip of the shaft. Each control cable is disposed opposite to its pair, and the control cables move in opposition to one another such that as one control cable is being pulled, the other is being released. The effect is to bend the tip of the shaft in a desired direction. In many endoscopes or catheters, the control cables have an outer sheath and an inner core wire. The outer sheath acts to transmit the longitudinal motion of the core wire to the distal tip of the endoscope. During a medical procedure, it is not uncommon for the shaft to form one or more loops as it is navigated to the tissue of interest. When a shaft including a control cable is looped, the outer sheath becomes increasingly stiff and harder to navigate within the body. At every bend of the shaft, the distances traveled by the core wire and its respective outer sheath differ, producing tension in the outer sheath and/or the core wire and increasing the amount of force needed to exert longitudinal force in the pull wire. This results in the user having less control over the tip of the device and less ability to detect external forces acting on the tip. Therefore, there is a need for a navigation system for use in steerable medical instruments that is still steerable at low forces if looped in the body.

SUMMARY

The present invention is an elongated medical instrument including a shaft that is steerable in a desired direction. Control cables in the shaft include an outer sheath and an inner core wire that is tensioned to articulate the distal tip of the shaft. To address the problems described above, the ends of the control cable are in contact with a steering system tension control device so that tension in the control cable created as a result of loops or bends in the shaft is relieved.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

As indicated above, the present invention is a device for relieving tension that occurs in control cables of steerable medical instruments as a result of loops and bends in the instrument. Although the disclosed embodiments are shown for use in an endoscope, it will be appreciated that the invention may be used in any steerable medical instrument, such as catheters for vascular, urological, and laparoscopic applications or the like.

Figure 1:
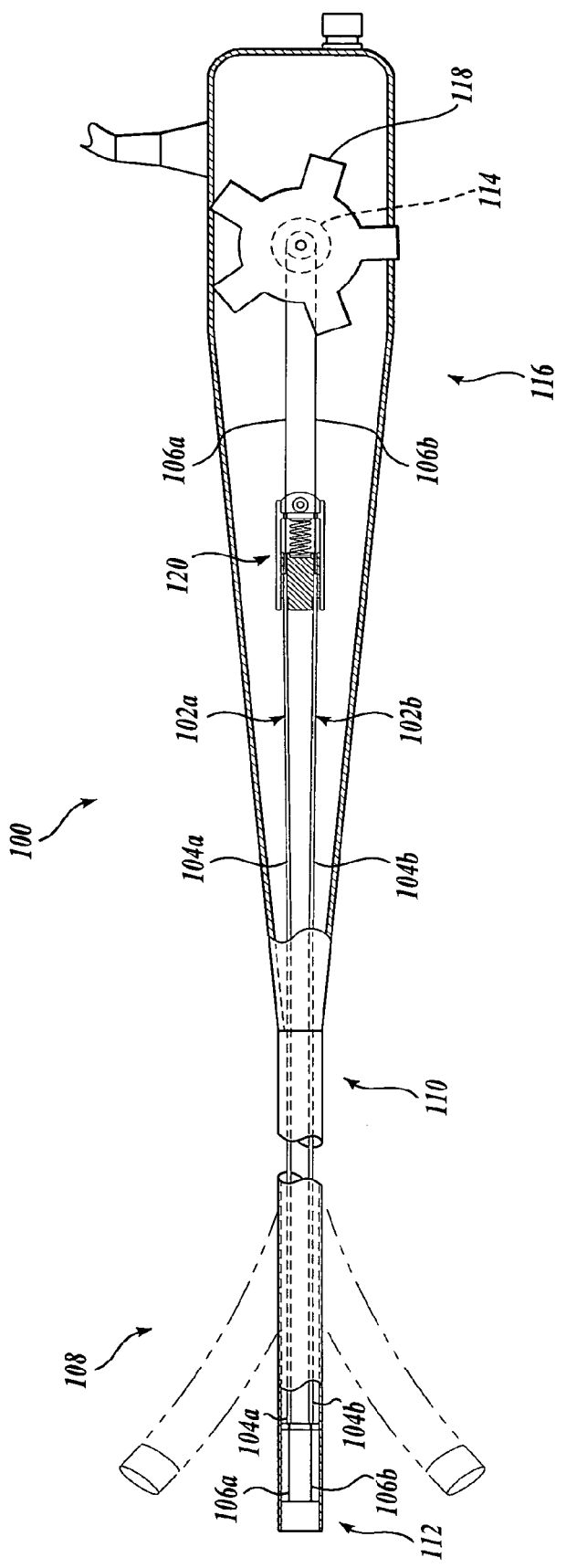
FIG. 1 is an illustration of an endoscope including a steering system tension control device according to an embodiment of the present invention.

FIG. 1 illustrates an endoscope 100 including a steering system tension control device 120 made in accordance with one embodiment of the present invention. Not all of the features of the endoscope 100 are being illustrated for brevity. The endoscope 100 includes a handle 116 that is connected to a shaft 108 having a proximal end 110 and a distal end 112. The handle 116 is connected to the proximal end 110 of the shaft 108. A pair of control cables 102a and 102b is used to steer the distal end 112 of the shaft 108. The control cables 102a and 102b each include a flexible and substantially incompressible outer sheath 104a and 104b, respectively, and a substantially constant length and flexible core wire 106a and 106b, respectively, which is positioned within the outer sheath 104a and 104b. The core wires 106a and 106b can be multi-strand wire or single strand wire. The outer sheaths 104a and 104b extend from a distal location of the shaft 108 to a proximal location and terminate within the interior of the handle 102. The core wires 106a and 106b are exposed beyond where the outer sheaths 104a and 104b end at the distal location and at the proximal location. The purpose for the outer sheaths 104a and 104b is generally to provide protection to the core wires 106a and 106b and to transmit the longitudinal movement of the core wires from the handle 116 to the distal tip of the shaft 108. The outer sheaths 104a and 104b can be a spiral wound material. Stainless steel is a suitable material for the outer sheaths 104a and 104b and the core wires 106a and 106b. A control cable having a core wire capable of sliding within an outer sheath is typically referred to as a "bowden" cable. The outer sheaths 104a and 104b are rigidly affixed at a distal location within the interior of the shaft 108. The outer sheaths 104a and 104b terminate at a proximal location within the interior of the handle 116 in a steering system tension control device 120, as discussed further below.

The core wires 104a and 104b extend from the distal tip 112 of the shaft 108 to a spool 114 within the interior and at the proximal end of the handle 116. The spool 114 is connected to a rotatable knob dial 118 that is exterior to the handle 116. The dial 118 can be turned clockwise or counterclockwise to rotate the spool 114. The distal ends of the core wires 106a and 106b are secured to the distal tip 112 of the shaft 108. The proximal ends of the core wires 106a and 106b are connected to the spool 114. For example, the core wires 106a and 106b may be connected at opposite tangents on the spool 114. Alternatively, the core wires 106a and 106b can be looped one or more times around the spool 114. In one embodiment, the core wires 106a and 106b can be the halves of a unitary core wire that loops around the spool 114. In yet another embodiment, the core wires 106a and 106b are distinct control cables that are separately attached to the spool 114. The core wires 106a and 106b can be attached to the distal tip 112 and to the spool 114 via an enlarged head or a barrel-like member, similar to a bicycle brake cable, that is inserted within a mating slot that enables the core wires to be removed. The core wires 106a and 106b are free to slide within the respective outer sheaths 104a and 104b according to the rotation of the dial 118 and the spool 114. The rotation of the dial 118 and spool 114 results in one or more of the core wires being tensioned. For example, in FIG. 1, by rotating the dial 118 clockwise, the core wire 106b is released, and the core wire 106a is tensioned. Therefore, core wire 106a pulls on the distal tip 112, while the core wire 106b is released to allow the distal tip 112 to bend. By selectively tensioning one or more of the core wires at the distal tip 112, the distal end of the shaft 108 will bend in the direction corresponding to the tensioning forces. If the entire length of the shaft 108 is straight and does not have any bends in it, the friction of the core wires 106a and 106b against the outer sheaths 104a and 104b is generally minimized. If, however, bends and entire loops are formed in the shaft 108, which is not uncommon in actual use, the shaft 108 may become difficult to steer due to the increase in tension as a result of the differences in the distances that the outer sheaths and core wires must travel around the bends or loops and the friction between the outer sheaths 104a and 104b and the core wires 106a and 106b. The tension in the cables acts as a "holding" force on the bending tip. Friction force increases exponentially with loops. The steering force required is the product of the force to overcome the friction of the loops by the holding force on the tip per the Capstan equation. Without intending to be bound by theory, it is believed that the additional tension under which the control cables are placed when under significant bending increases exponentially with the amount of bending. The increase in tension is governed by the Capstan equation. Although the embodiments of the present invention are useful to relieve tension of applications utilizing a single control cable, the tension relieving devices described herein preferably operate with a "closed system" of cables, i.e., a pair of control cables. In a pair of control cables, the front cable is designated as the cable that is being pulled, while the back cable is designated the cable that needs to be released. It is believed that the tension in the back cable substantially adds to the force required to bend the tip, because the back cable has to travel a greater path when the tip is bent, since the back cable is at the outer radius of the bend. Significant tension on the back cable adds to what is termed "holding" force, which is the bending stiffness of the tip. As part of the solution of relieving the tension in the control cables, embodiments of the tension control devices in accordance with the present invention keep the tensions low in the cables even when under significant bending, such as by allowing the outer sheath of the cables to compress against a spring, thereby, unloading the holding force within the closed system.

Figure 2:
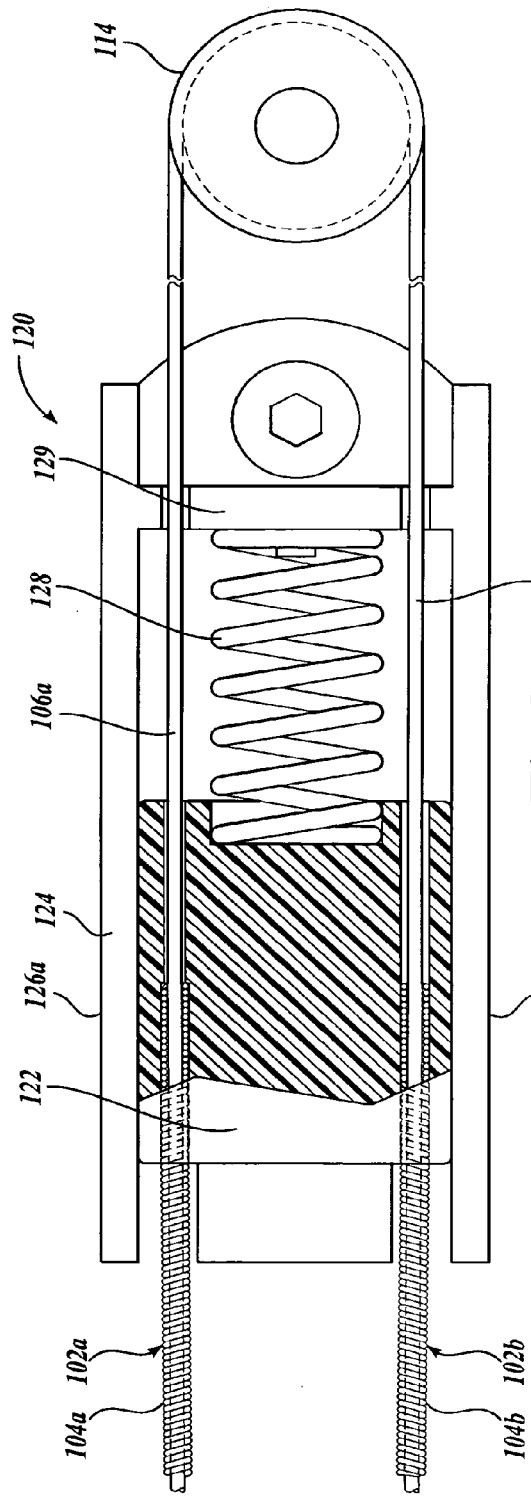
FIG. 2 is an illustration of one embodiment of a steering system tension control device according to the present invention.

In order to relieve tension in the cables, one embodiment of the invention includes a steering system tension control device 120. As best seen in FIG. 2, the steering system tension control device 120 includes a slide block 122, which is disposed in a sliding engagement within a constraining structure 124. The slide block 122 is a pressure transfer member that transfers the pressure imparted by an outer sheath to a spring. The slide block 122 is one implementation of the pressure transfer member. In some embodiments, the pressure transfer member, or slide block 122, can be omitted so that direct contact is made between the outer sheath and the spring. The slide block 122 has a number of apertures for each respective control cable 102a and 102b. Each aperture has a first relative large diameter through which the outer sheaths 104a and 104b can pass. Each aperture includes a second, narrower diameter through which only the core wires 106a and 106b can pass. In this manner, the ends of the outer sheaths 104a and 104b can abut against the shoulders created between the first and second diameters to push on the slide block 122. The slide block 122 travels within the confines of the constraining structure 124. A constraining structure 124 can have two side walls 126a and 126b between which the slide block 122 is retained that allows the slide block 122 to travel in a linear path. The side walls 126a and 126b can be attached to one half of the handle 118 housing (not shown), or alternatively, the side walls 126a and 126b can be molded directly as part of the handle 118 housing. The second half of the handle 118 housing (not shown) has features corresponding to the constraining structure 124, such that when the second half of the handle 118 housing is mated to the first, the slide block 122 is restrained on four sides by the sidewalls 126a and 126b and by the first and second halves of the handle 118 housing.

A compression spring 128 is placed in contact with the slide block 122 on the opposite side to the outer sheaths 104a and 104b. The opposite end of the spring 128 rests against an immovable abutment 129. Alternatively, the spring 128 can be connected to a roller (cam follower) which is in contact with a cam surface as further described below. When one or both outer sheaths 104a and 104b are under compression (due to looping or significant bending of the shaft) sufficient to overcome the counteracting force of the spring 128, the slide block 122 will give and slide to compress the spring 128. Such action relieves the compression on one or both of the outer sheaths 104a and 104b, relieving the tension on the core wires 106a and 106b and making them easier to move. The tension in the core wires 106a and 106b is not allowed to exceed a predetermined limit that is set by the counteracting force of spring 128. The spring 128 stiffness is selected so that it can withstand (without compression) the tension applied to the core wires 106a and 106b by the user during regular steering to bend the tip (especially at low looping configurations), but will compress when, for example, four cables are looped, or significantly bent, to relieve the tension.

The slide block 122 and the surfaces of the walls against which the slide block 122 slides can be made from, or covered with, a naturally lubricious material, such as a polyfluorocarbon polymer, such as polytetrafluoroethylene (TEFLON®) or a polyamide to reduce the friction between the slide block 122 and the sliding surfaces.

While the steering system tension control device 120 is illustrated as being located in the handle 116 of the endoscope and has a spring 128 to act against the proximal ends of the outer sheaths 104a and 104b, an alternative embodiment can have one or more springs that act against the distal ends of the outer sheaths 104a and 104b at the distal end of the shaft. The spring stiffness is designed to compress during shaft looping or bending and relieve tension in the core wires 106a and 106b. Furthermore, the outer sheaths 104a and 104b can be divided into two or more sections from the distal location to the proximal location. One or more springs can be disposed in the "breaks" between sections of the outer sheaths. In such configurations, each section of the outer sheath has intermediate ends against which a spring can be disposed to act against and between two sections of the same control cable. Several springs, therefore, can be disposed on a single control cable. Furthermore, a helical spring is a representative spring. Alternative springs include leaf springs, elastomer materials, gas or fluid-filled chambers with pistons, compressed air chambers, or the like having characteristic spring-like behavior.

Although the embodiment shown in FIG. 2 uses a single spring for all of the control cables, it will be appreciated that it is possible to use multiple springs, such as a single spring per control cable wherein the core wire is passed through the center of the spring such that the end of the spring can rest against the end of the outer sheath. The opposite end of the spring would then rest against a fixed support. It is possible to also have more than one spring per control cable and more than one control cable per spring. Furthermore, springs can be disposed at any location along the length of the control cable, including the proximal and distal ends and also at intermediate ends where the control cable is divided into more than one section. The distal, proximal, or intermediate spring configurations have the ability to relieve tension in the control cable or cables and allow compression of a spring when the compression due to looping of the outer sheath exceeds the counteracting force of the spring.

In another embodiment, the outer sheath can be made from a tightly wound coil material. Therefore, one inexpensive method of placing springs in one or various sections of the sheath is to wind a coil with variable pitch at locations in the coil that can be used for the sheath and the spring or springs by separating the loops of the coil. For example, the windings of the outer sheath may be spread apart to form a compressible spring that compresses under the force built up as the outer sheath is lodged within the body. In this embodiment, the windings of the outer sheath also act as springs in addition to or as an alternative to the slide block and spring configuration.

While FIGS. 1 and 2 illustrate a first and a second control cable, it is to be appreciated that the present invention can be implemented using any number of control cables, from at least one control cable to as many as desired. In a steering system with one control cable, for example, the single control cable can be configured with a return spring. The return spring applies constant tension to continually bias the distal tip in one direction, while the single control cable is actuated to bias the distal tip in the opposite direction. Any steering system with an odd or even number of control cables can be utilized. In systems having an even number of control cables, two control cables can be paired to act against one another. Having more than one pair of control cables can necessitate the use of an additional spool and corresponding dial on the handle.

Figure 3:
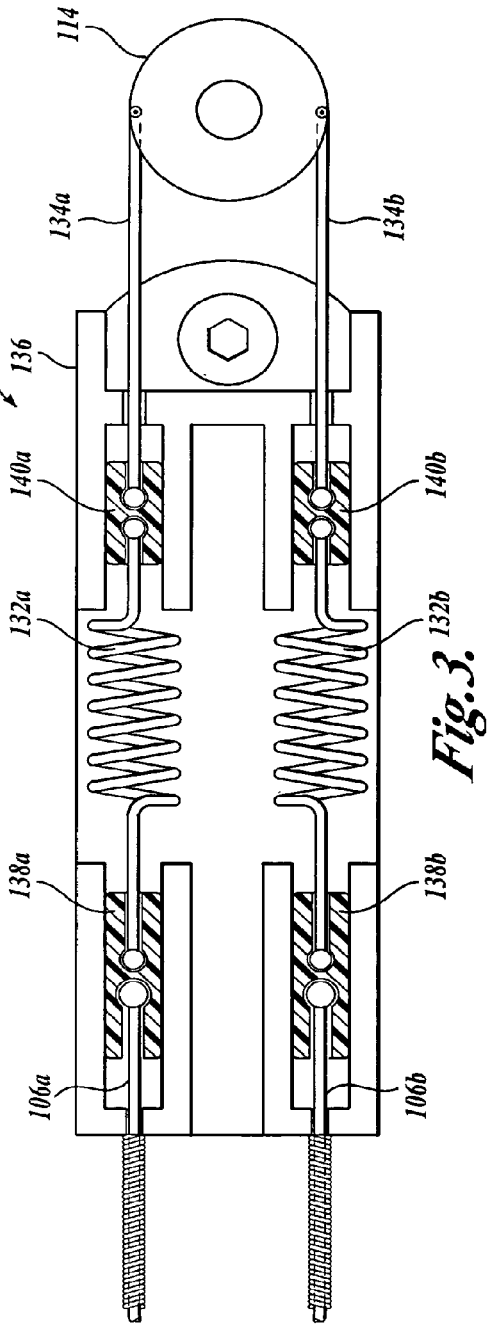
FIG. 3 is an illustration of another embodiment of a steering system tension control device in accordance with the present invention.

FIG. 3 illustrates another embodiment of a steering system tension control device in accordance with the present invention. In certain situations, the core wire of each of the control cables 102a and 102b can also have tension relief. In this embodiment, the core wires 106a and 106b are connected to a spring 132a and 132b, respectively, to provide tension relief for the core wire instead of, or in addition to, a spring that provides for compression relief on the outer sheaths 104a and 104b. In this embodiment, each core wire 106a and 106b is connected to a first slide block 138a and 138b, respectively.

The slide blocks 138a and 138b are further connected to the springs 132a and 132b, respectively. The springs 132a and 132b are connected to a second set of slide blocks 140a and 140b, respectively, and the slide blocks 140a and 140b are connected to short sections of wire 134a and 134b, respectively, which are ultimately connected to the spool 114 in the manner described above. Therefore, in this embodiment, if there is excessive tension on the core wires 106a and 106b, the tension can be relieved by the springs 132a and 132b. In this case, the springs 132a and 132b work, not in compression, but in expansion to relieve tension. Generally, the spring constant of springs 132a and 132b should be fairly high so as to avoid excessive play when the steering control dial 118 is turned, and so that the distal tip 112 articulates even for small movements of the dial 118. The tension relief on the core wires 106a and 106b is in addition to or, alternatively, as a substitute for, compression relief on the outer sheaths 104a and 104b. The tension springs 132a and 132b should be of adequately high stiffness to avoid any elongation at low looping configurations. However, the springs 132a and 132b should elongate as required to reduce tension when loops build up in the core wires 106a and 106b.

Figure 4:
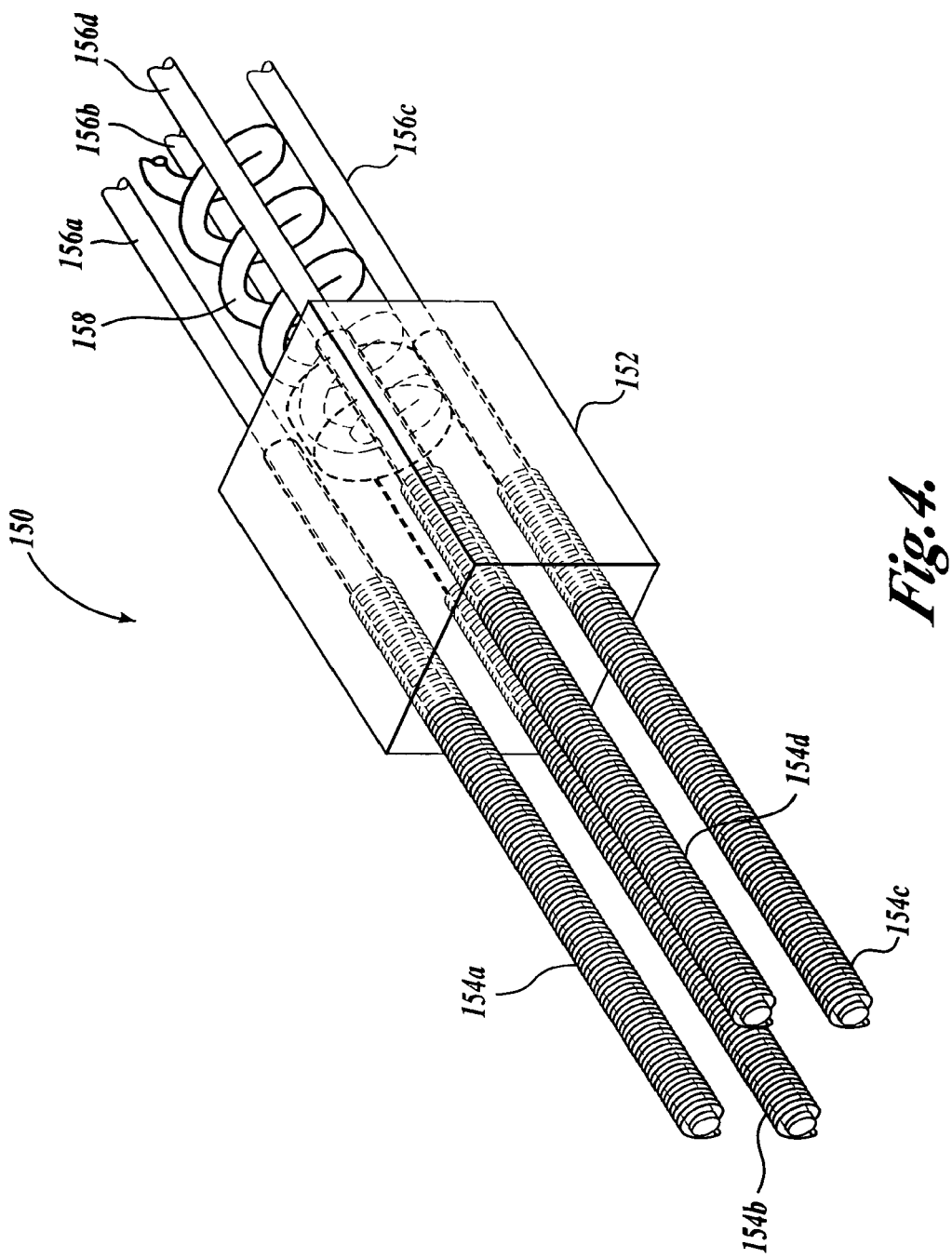
FIG. 4 is an illustration of another embodiment of a steering system tension control device in accordance with the present invention.

FIG. 4 illustrates another embodiment of a steering system tension control device in accordance with the present invention. It is often desirable to have four degrees of freedom when steering the distal tip 112 of the endoscope shaft 108. To this end, two pairs of control cables are used. A single slide block 152 can be made to accept four control cables 154a, 154b, 154c, and 154d, wherein the outer sheath of each control cable 154a, 154b, 154c, and 154d is made to abut against the slide block 152, but with the core wires 156a, 156b, 156c, and 156d passing through the slide block 152. Each core wire 156a, 156b, 156c, and 156d is connected to one of two spools with its respective paired core wire. In this embodiment, a central spring 158 abuts against the slide block 152 to provide for tension relief in any one or all of the four outer sheaths of the four control cables 154a, 154b, 154c, and 154d. The embodiment of FIG. 4, in addition to other spring configuration embodiments can also be provided at the distal end of the outer sheaths so that the spring 158 is disposed to act against the proximal ends of the outer sheaths, or alternatively, between sections of the outer sheaths so that the spring 158 is disposed to act against ends in the outer sheath that are between the proximal end of the outer sheath and the distal end of the outer sheath. The spring 158 can be rigidly affixed at the end opposite to the slide block 152, or the spring 158 can be connected to a roller which is in contact with a cam surface as further described below.

It is also appreciated that the spring is acting as a compressible member. A less expensive version of the design involves a compressible block made of polypropylene, or similar material, in the handle of the device to anchor the outer sheaths. The thickness of the block and the durometer of the material can be adjusted to give the required elastic compression/deflection to relieve tension on the control cables during looping or significant bending of the shaft.

Figure 5:
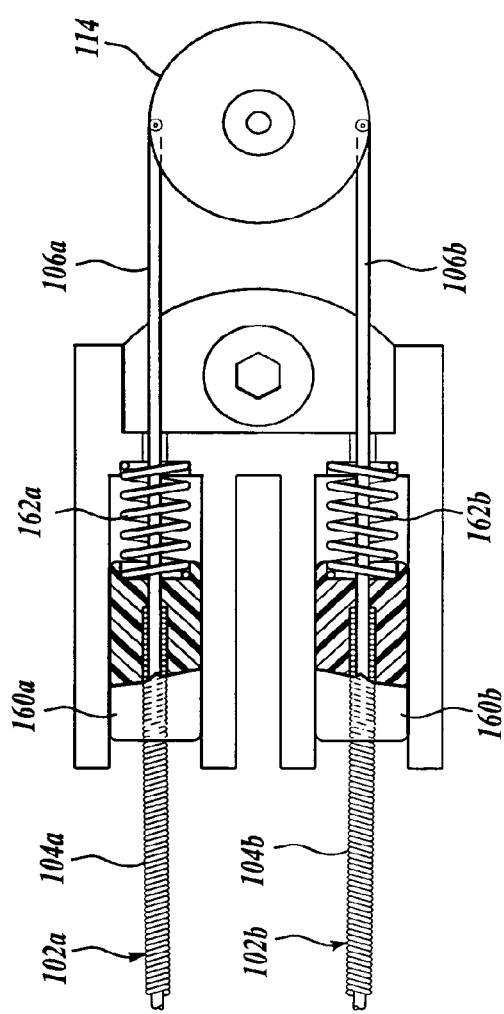
FIG. 5 is an illustration of another embodiment of a steering system tension control device according to the present invention.

FIG. 5 illustrates another embodiment of a steering system tension control device in accordance with the present invention. In this embodiment, slide blocks 160a and 160b are provided for control cables 102a and 102b, respectively. Slide blocks 160a and 160b abut against springs 162a and 162b, respectively. As with the other embodiments, the slide blocks 160a and 160b accept the outer sheaths 104a and 104b that abut against the slide blocks 160a and 160b, but the core wires 106a and 106b are allowed to pass through the respective slide blocks 160a and 160b. The springs 162a and 162b may be fixed rigidly, as shown, or each spring 162*a* and 162*b* can be connected to a roller in contact with a cam surface as described below.

Figure 6:
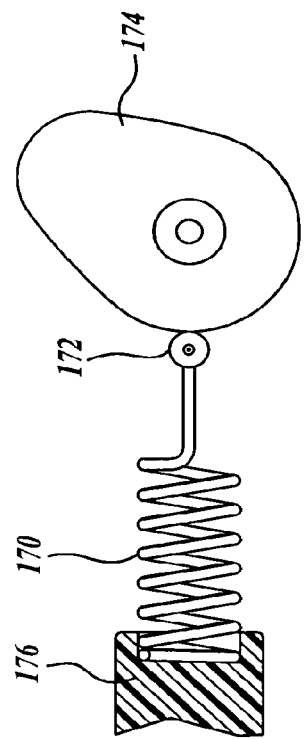
FIG. 6 is an illustration of another embodiment of a steering system tension control device according to the present invention.

FIG. 6 illustrates another embodiment of a steering system tension control device having a cam system in accordance with the present invention. The end of any spring thus far described that is opposite to a slide block 176 is connected to a roller 172 (cam follower). The roller 172 can rotate about its axis, but can also translate linearly. Thus, with translation of the roller 172 forwards and backwards, the amount of spring 170 compression can be adjusted. The roller 172 is in contact with a surface of a lobed cam 174. The cam 174 may be connected to a dial or a lever (not shown) that is manipulated from the outside of the handle 116 to rotate the cam 174. Rotation of the cam 174 therefore, causes the roller 172 to translate linearly forwards and backwards depending on the position of the cam 174. For example, as illustrated, the roller 172 and cam 174 are in contact with each other when the radius from the axis of the cam 174 to the contact point with the roller 172 is at its shortest distance. However, when the cam 174 is rotated in a counterclockwise direction, the radius from the axis of rotation of the cam 174 to the contact point will increase, thus pushing the roller 172 against the spring 170, which in turn compresses the spring 170 and applies a greater force on the slide block 176. This embodiment can adjust the amount of tension for any particular situation with the turn of a dial. For example, in high looping configurations, the spring 170 can be adjusted to the lowest spring compression setting (as illustrated) to allow for the maximum tension relief. In low looping configurations, the cam 174 can be rotated to the highest spring compression setting and provide the least amount of tension relief and ensure no deadband in the response of the tip. The cam's 174 surface in contact with the roller 172 can be shaped to give an exponential increase in the spring's 170 stiffness. Alternatively, the increase in the stiffness can be linearly related to the cam's 174 surface. The physician can rotate the dial to any position therebetween to reduce tension in the control cables as loops build up in the shaft during a procedure. As the physician begins to feel the tension increasing in the control dial, the physician can adjust the cam and reduce the forces. As the physician withdraws the shaft and removes the loops, he could then rotate the dial in the opposite direction and take up the slack again. An additional advantage of this embodiment is that it allows physicians to adjust the tightness of the steering system and, hence, their ability to detect external forces acting on the tip, based on their particular preference.

Another embodiment of this design has the sliding block that anchors the outer sheaths connected directly to the cam without a spring. By rotating a lever on the outside of the handle, the physician can control the location of the block and, hence, the tension in the steering cables.

The stiffness of a spring of any outer sheath or core wire of the embodiments described above can be calculated through designs of experiments by conducting testing at low and high looping configurations. To gauge a suitable spring stiffness, the following general guidelines are provided.

About 20° of play on the dial 118 appears to be the limit that is acceptable to most physicians. A suitable shaft has very little, if any, looseness in the control cables at low looping configurations and prevents tension from building up to ensure low steering torques at high looping configurations (2¼ to 3 loops, where each loop is 360°). A suitable compression spring is designed to compress and compensate for the increase in length of the outer sheath as more bends are made in the shaft to substantially keep the core wire path length constant. During low looping configurations, the compression spring is stiff enough to withstand the articulation forces transmitted through the steering dial(s). One optimum spring stiffness appears to be in the range of about 60 lbs./in. to about 100 lbs./in. It can be appreciated that the optimum spring stiffness can depend on many factors, such as, the bending stiffness of the tip, the stiffness of the outer sheath and core wire combined, and the number of loops expected during a procedure.

While illustrative embodiments have been illustrated and described, it will be appreciated that various changes can be made therein without departing from the scope of the invention. Therefore, the present invention is to be determined from the following claims and equivalents thereof.

The embodiments of the invention in which an exclusive property or privilege is claimed are defined as follows:

1. A control device for a medical instrument having a shaft, comprising:
   (a) a first control cable disposed within the shaft of the medical instrument, wherein the first control cable is configured to be selectively tensioned to steer a tip of the medical instrument, the first control cable having a first elongate member surrounded by a first outer sheath;
   (b) a first spring disposed to exert a biasing force in a distal direction against a proximalmost end of the first outer sheath, and reduce a force in the first outer sheath caused by a first bend in the shaft;
   (c) a second control cable disposed within the shaft of the medical instrument, wherein the second control cable is configured to be selectively tensioned to steer the tip of the medical instrument, the second control cable having a second elongate member surrounded by a second outer sheath; and
   (d) a second spring disposed to reduce a force in the second outer sheath caused by a second bend in the shaft, wherein the first spring is independently moveable relative to the second spring, and the first control cable and the second control cable control movement of the shaft in opposing directions.

2. The control device of claim 1, wherein at least one of the first spring and the second spring is a compression spring.

3. The control device of claim 1, further comprising a cam follower disposed on the end of at least one of the first spring and the second spring, wherein the cam follower is in contact with a cam, wherein rotation of the cam changes the compression of the at least one of the first spring and the second spring.

4. The control device of claim 1, wherein at least one of the first outer sheath and the second outer sheath comprises a spiral wound material.

5. The control device of claim 4, wherein at least one of the first spring and the second spring is formed from the spiral wound material that also forms the corresponding outer sheath.

6. The control device of claim 1, wherein movement of the first outer sheath away from the tip causes compression of the first spring.

7. The control device of claim 1, wherein the first elongate member passes through the first spring.

8. The control device of claim 1, wherein the opposing directions are substantially coplanar.

9. The control device of claim 1, further including a slide member coupled to the first spring and the first outer sheath.

10. The control device of claim 9, wherein the slide member directly engages the proximalmost end of the first outer sheath.

11. The control device of claim 10, wherein the proximalmost end of the first outer sheath is within the slide member.

12. A control device for a medical instrument having a shaft, comprising:
(a) a first control cable disposed within the shaft of the medical instrument, wherein the first control cable is configured to be selectively tensioned to steer a distal tip of the medical instrument, the first control cable having a first elongate member surrounded by a first outer sheath;
(b) a first spring disposed to exert a biasing force in a distal direction against a proximalmost end of the first outer sheath, and reduce a force in the first outer sheath caused by a first bend in the shaft, wherein movement of the first outer sheath away from the tip causes compression of the first spring;
(c) a second control cable disposed within the shaft of the medical instrument, wherein the second control cable is configured to be selectively tensioned to steer the tip of the medical instrument, the second control cable having a second elongate member surrounded by a second outer sheath; and
(d) a second spring disposed to reduce a force in the second outer sheath caused by a second bend in the shaft, wherein the first spring is independently moveable relative to the second spring.

13. The control device of claim 12, wherein the first spring includes a moveable distal end configured to move with the proximalmost end of the first sheath, and a substantially stationary proximal end.

14. The control device of claim 12, further including a slide member coupled to the first spring and the first outer sheath, wherein the proximalmost end of the first outer sheath terminates within the slide member.

15. A control device for a medical instrument having a shaft, comprising:
a first control cable disposed within the shaft of the medical instrument, wherein the first control cable is configured to be selectively tensioned to steer a tip of the medical instrument, the first control cable having a first elongate member surrounded by a first outer sheath;
a first spring disposed to reduce a force in the first outer sheath caused by a first bend in the shaft;
a first slide member coupled to the first spring, wherein a proximal end of the first outer sheath terminates in the first slide member;
a second control cable disposed within the shaft of the medical instrument, wherein the second control cable is configured to be selectively tensioned to steer the tip of the medical instrument, the second control cable having a second elongate member surrounded by a second outer sheath; and
a second spring disposed to reduce a force in the second outer sheath caused by a second bend in the shaft, wherein the first spring is independently moveable relative to the second spring, and the first control cable and the second control cable control movement of the shaft in opposing directions.

16. The control device of claim 15, wherein a distal end of the first spring engages the first slide member.

17. The control device of claim 15, wherein the first outer sheath and the first slide member are coaxial.

18. The control device of claim 15, further including a second slide member coupled to the second spring, wherein a proximal end of the second outer sheath terminates in the second slide member.

* * * * *